United States Patent
Sheves et al.

(10) Patent No.: US 10,030,224 B2
(45) Date of Patent: Jul. 24, 2018

(54) METHODS OF ANALYZING CELL MEMBRANES

(71) Applicants: Ariel-University Research and Development Company Ltd., Ariel (IL); Yeda Research and Development Co. Ltd., Rehovot (IL); Indian Institute of Technology Bombay, Mumbai (IN)

(72) Inventors: Mordechai Sheves, Rehovot (IL); Irishi N. N. Namboothiri, Mumbai (IN); Guy Patchornik, Kiryat-Ono (IL)

(73) Assignees: Ariel-University Research and Development Company Ltd., Ariel (IL); Yeda Research and Development Co. Ltd., Rehovot (IL); Indian Institute of Technology Bombay, Mumbai (IN)

( * ) Notice: Subject to any disclaimer, the term of this patent is extended or adjusted under 35 U.S.C. 154(b) by 0 days.

(21) Appl. No.: 14/929,363

(22) Filed: Nov. 1, 2015

(65) Prior Publication Data

US 2017/0121668 A1    May 4, 2017

(51) Int. Cl.
*C12N 1/00* (2006.01)
*C07K 14/215* (2006.01)

(52) U.S. Cl.
CPC .......... *C12N 1/005* (2013.01); *C07K 14/215* (2013.01)

(58) Field of Classification Search
None
See application file for complete search history.

(56) References Cited

FOREIGN PATENT DOCUMENTS

| WO | WO 2005/010141 | 2/2005 |
| WO | WO 2006/085321 | 8/2006 |
| WO | WO 2009/010976 | 1/2009 |

OTHER PUBLICATIONS

Patchornik et al., Bioconjugate Chemistry, 2013, vol. 24, p. 1270-1275.*
Harlow et al., CSH Protoc., 2006, vol. 4, p. 625-626, Abstract Only.*
Marechel et al., The Journal of Biological Chemistry, 1995, vol. 270, No. 11, p. 5714-5722.*
Dutta et al. "Engineered-Membranes and Engineered-Micelles as Efficient Tools for Purification of Halorhodopsin and Bacteriorhodopsin", The Analyst, 140(1): 204-212, Nov. 3, 2014.
Patchornik et al. "Engineered-Membranes: A Novel Concept for Clustering of Native Lipid Bilayers", Journal of Colloid and Interface Science, 388: 300-305, Available Online Aug. 28, 2012.
Patchornik et al. "Tethered Non-Ionic Micelles: A Matrix for Enhanced Solubilization of Lipophilic Compounds", Soft Matter, 8: 8456-8463, Published Online Jul. 5, 2012.

* cited by examiner

*Primary Examiner* — Kade Ariani

(57) ABSTRACT

A method of precipitating cell membrane fragments from a cell lysate is disclosed. The method comprises contacting the cell lysate with a hydrophobic chelator and a metal ion under conditions that allow precipitation of the cell membrane fragments. Kits for precipitating cell membrane fragments are also disclosed.

27 Claims, 2 Drawing Sheets

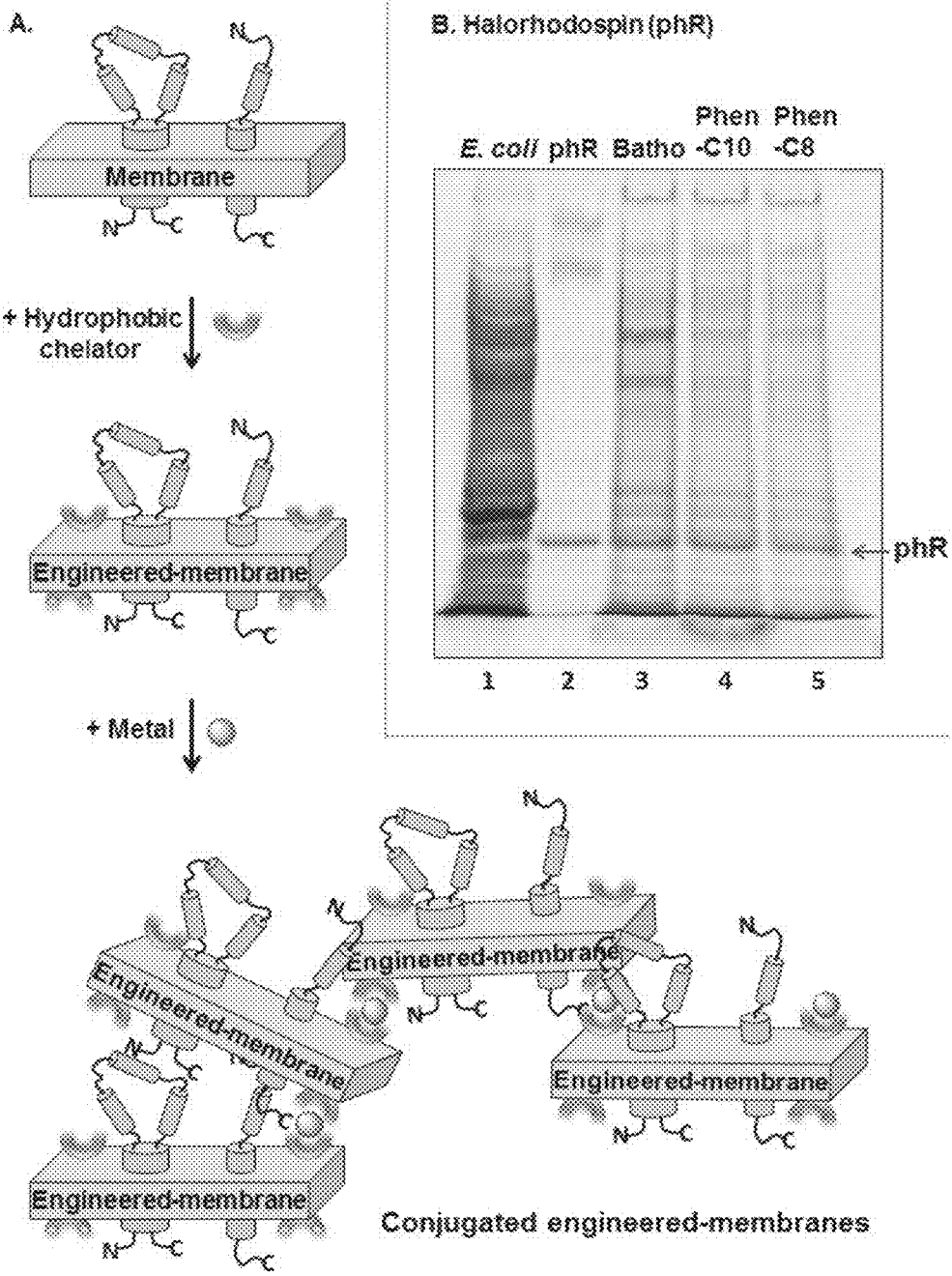

Figure 2A
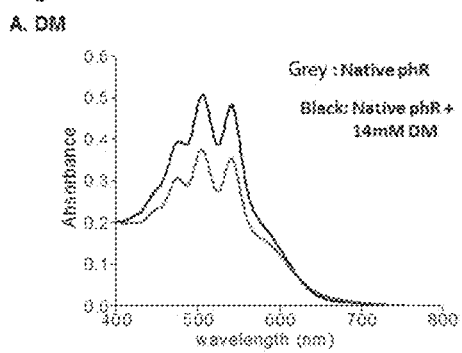
Figure 2B
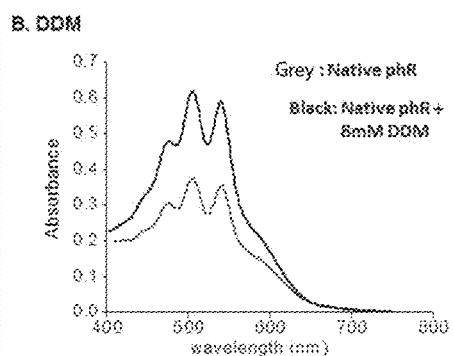
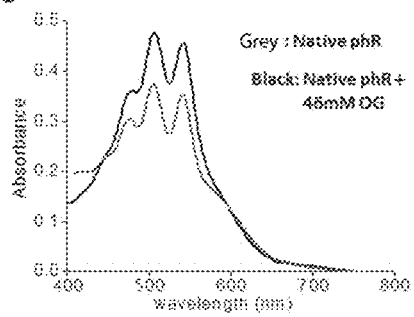
Figure 2C
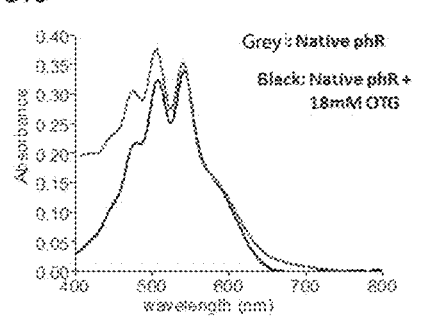
Figure 2D

METHODS OF ANALYZING CELL MEMBRANES

FIELD AND BACKGROUND OF THE INVENTION

The present invention, in some embodiments thereof, relates to methods and, kits for isolating membrane proteins.

Isolation of membrane proteins (MPs) in a pure, concentrated and functional state is a precondition for structural determination by X-ray crystallography, electron microscopy or nuclear magnetic resonance (NMR).

Extraction of membrane proteins from the membrane of a cell in which they are expressed may be achieved by addition of detergents at concentrations greater than their critical micellar concentration (cmc). Under these conditions, the detergent disrupts the membrane and, in parallel, surrounds and covers the hydrophobic domains of the protein, leading to formation of water-soluble [detergent-MP-lipid] ternary complexes. Purification is accomplished either via classical chromatographic methods (e.g. ion exchange chromatography) or by genetically engineered affinity-tags (e.g. His-tag) which can lead to highly pure protein preparations. Clearly, exclusion of other (non-membrane) cellular proteins by non-chromatographic means prior to the chromatographic step, would simplify purification and potentially lead to higher recovery yields and overall greater purity.

In 1981, Bordier demonstrated that MPs (being hydrophobic) partition efficiently into detergent-rich phases composed of the non-ionic detergent Triton X-114, whereas water-soluble proteins do not. This partitioning process, called cloud point extraction, relied on the ability of Triton X-114 to undergo phase separation at ~22° C. into detergent-rich and detergent-poor phases. Although Triton X-114 provided working conditions that could preserve the functionality of many MPs, the approach was limited by the fact that numerous other detergents, commonly used in the purification of membrane proteins, only reach the cloud point at elevated temperatures that would denature most proteins. Successful attempts to lower the cloud point temperature in the presence of high concentrations of water-soluble polymers have been reported. However, it is clear that purification would be greatly simplified if neither polymers nor precipitants were required.

Background art includes Patchornik et al., Journal of Colloid and Interface Science 388 (2012) 300-305; and Patchornik et al., Soft Matter, 2012, 8, 8456.

Additional background art includes WO2005/010141, WO2006/085321 and WO2009/010976.

SUMMARY OF THE INVENTION

According to an aspect of some embodiments of the present invention there is provided a method of precipitating cell membrane fragments from a cell lysate, the method comprising contacting the cell lysate with a hydrophobic chelator and a metal ion under conditions that allow precipitation of the cell membrane fragments.

According to an aspect of some embodiments of the present invention there is provided a kit for precipitating cell membrane fragments comprising a hydrophobic chelator, a metal ion and at least one protease inhibitor.

According to an aspect of some embodiments of the present invention there is provided a method of purifying a membrane protein comprising:

(a) precipitating cell membrane fragments which comprise the membrane protein from a cell lysate according to the method described herein;
(b) isolating the cell membrane fragments following the precipitating; and
(c) solubilizing the membrane protein, thereby purifying the membrane protein.

According to an aspect of some embodiments of the present invention there is provided a composition of matter comprising a N-(1,10-Phenanthrolin-5-yl)alkylamide), wherein the alkyl is being from 1-9 carbon atoms in length.

According to some embodiments of the invention, the cell membrane fragments are generated by sonicating whole cells.

According to some embodiments of the invention, the cell lysate is a whole cell lysate.

According to some embodiments of the invention, the cell lysate is devoid of organelles greater than about 2 microns.

According to some embodiments of the invention, the method further comprises isolating the cell membrane fragments from the cell lysate following the precipitating.

According to some embodiments of the invention, the method further comprises solubilizing proteins of the cell membrane fragments following the isolating.

According to some embodiments of the invention, the solubilizing is effected with a detergent.

According to some embodiments of the invention, the detergent comprises a non-ionic detergent.

According to some embodiments of the invention, the detergent is selected from the group consisting of decyl β-D-maltoside (DM), dodecyl β-D-maltoside (DDM), octyl β-D-glucoside (OG) and octyl β-D-1-thioglucoside (OTG).

According to some embodiments of the invention, the contacting is effected in the absence of a detergent.

According to some embodiments of the invention, the hydrophobic chelator comprises 8-Hydroxyquinoline.

According to some embodiments of the invention, the hydrophobic chelator comprises a phenanthroline.

According to some embodiments of the invention, the phenanthroline is selected from the group consisting of N-(1,10-Phenanthrolin-5-yl)methanamide) (Phen-C1), N-(1,10-Phenanthrolin-5-yl)ethanamide) (Phen-C2), N-(1,10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), N-(1,10-Phenanthrolin-5-yl)nonanamide) (Phen-C9) and N-(1,10-Phenanthrolin-5-yl)decanamide) (Phen-C10).

According to some embodiments of the invention, the phenanthroline is selected from the group consisting of bathophenanthroline, N-(1,10-Phenanthrolin-5-yl)hexanamide) (Phen-6), N-(1,10-Phenanthrolin-5-yl)decanamide) (Phen-C10) and N-(1,10-Phenanthrolin-5-yl)octanamide) (Phen-C8).

According to some embodiments of the invention, the phenanthroline is selected from the group consisting of Phen-C10 and Phen-C8.

According to some embodiments of the invention, the metal ion is a divalent metal ion.

According to some embodiments of the invention, the divalent metal ion is selected from the group consisting of $Zn^{2+}$, $Fe^{2+}$, $Mn^{2+}$, $Ni^{2+}$ and $Co^{2+}$.

According to some embodiments of the invention, the divalent metal ion is selected from the group consisting of $Zn^{2+}$ and $Fe^{2+}$.

According to some embodiments of the invention, the contacting the cell lysate with a hydrophobic chelator is effected prior to the contacting the cell lysate with a metal ion.

According to some embodiments of the invention, the cell membrane fragments have a length ranging between 200-700 nm.

According to some embodiments of the invention, the cell lysate is further contacted with a hydrophilic chelator following or concomitant with the contacting with the hydrophobic chelator.

According to some embodiments of the invention, the kit further comprises a hydrophilic chelator.

According to some embodiments of the invention, the hydrophilic chelator is selected from the group consisting of ethylenediaminetetraacetate (EDTA), ethylene glycol tetraacetate (EGTA), histidine and analogues thereof.

According to some embodiments of the invention, the hydrophilic chelator comprises ethylenediaminetetraacetate (EDTA).

According to some embodiments of the invention, the hydrophobic chelator is present in the aqueous solution at a concentration in the range of about 5% to about 10% (v/v).

According to some embodiments of the invention, the metal ion is present in the aqueous at a concentration in the range of about 5% to about 10% (v/v).

According to some embodiments of the invention, the cell lysate is derived from a bacterial cell.

According to some embodiments of the invention, the cell lysate is derived from an archaeal cell.

According to some embodiments of the invention, the archaeal cell is a *halobacterium* cell.

According to some embodiments of the invention, the *halobacterium* is selected from the group consisting of *Halobacterium salinarum*, *Haloferax denitrificans*, *Alorubrum distributum*, *Alobacterium salinarum*, *Halobacterium jilantaiense*, *Halorubrum lacusprofundi*, *Haloferax mediterranei*, *Halobacterium noricense*, *Natronomonas pharaonis*, *Halobacterium piscisalsi*, *Halorubrum saccharovoru*, *Halobacterium salinarum*, *Halorubrum sodomense*, *Halorubrum trapanicum*, *Haloarcula vallismortis* and *Halobacterium volcanii*.

According to some embodiments of the invention, the solubilizing is effected using a detergent.

According to some embodiments of the invention, the detergent is a non-ionic detergent.

According to some embodiments of the invention, the detergent is selected from the group consisting of decyl β-D-maltoside (DM), dodecyl β-D-maltoside (DDM), octyl β-D-glucoside (OG) and octyl β-D-1-thioglucoside (OTG).

According to some embodiments of the invention, the isolating comprises:

(a) centrifuging the cell lysate to form a pellet comprising the cell membrane fragments and a supernatant; and (b) removing the supernatant from the pellet.

According to some embodiments of the invention, the membrane protein is a retinyledene protein.

According to some embodiments of the invention, the retinyledene protein is selected from the group consisting of channelrhodopsin, bacteriorhodopsin, halorhodopsin, and proteorhodopsin.

According to some embodiments of the invention, the retinyledene protein comprises halorhodopsin.

According to some embodiments of the invention, the halorhodopsin is derived from *Natronomonas pharaonis*.

According to some embodiments of the invention, the N-(1,10-Phenanthrolin-5-yl)alkylamide) is selected from N-(1,10-Phenanthrolin-5-yl)methanamide) (Phen-C1), N-(1,10-Phenanthrolin-5-yl)ethanamide) (Phen-C2), N-(1,10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), and N-(1,10-Phenanthrolin-5-yl)nonanamide) (Phen-C9).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1A is a schematic representation of the method disclosed herein according to embodiments of the present invention;

FIG. 1B shows sodium dodecyl sulfate polyacrylamide gel electrophoresis (SDS-PAGE) analysis of pellets purified according to the methods disclosed herein;

FIGS. 2A-2D show absorption spectra of Halorhodopsin after purification according to an embodiment of the teachings herein, and following dissolution with detergents decyl β-D-maltoside (DM) (FIG. 2A, "grey" or dashed is the lower trace), dodecyl β-D-maltoside (DDM) (FIG. 2B, "grey" or dashed is the lower trace), octyl β-D-glucoside (OG) (FIG. 2C, "grey" or dashed is the lower trace) or octyl β-D-1-thioglucoside (OTG) (FIG. 2D, "grey" or dashed is the trace that is higher on the left side).

DESCRIPTION OF SPECIFIC EMBODIMENTS OF THE INVENTION

The present invention, in some embodiments thereof, relates to methods and kits for precipitating cell membranes and in some embodiments to the purification of proteins expressed therein.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Purification of membrane proteins requires disruption of the cell membrane. Typically, this is carried out using detergents. However, such agents may be deleterious to the proteins, causing denaturation.

The present inventors have now conceived of a method of membrane disruption that does not require the use of detergents, requires no sophisticated instrumentation, is relatively rapid, is performed under mild conditions and is capable of removing the majority of non-membrane cellular proteins prior to a final chromatographic step.

The method entails contacting fragments of the membrane of the cell with a hydrophobic chelator and a metal ion—see FIG. 1A. This leads to aggregation of the membrane fragments containing the expressed membrane protein, resulting in precipitation of the protein-containing membrane from aqueous solution. Since the membrane protein is maintained in its native bilayer environment throughout the extraction process, the present inventors propose that disclosed method protects the membrane protein from denaturation.

Whilst reducing the present invention to practice, the present inventors, using the method described above, precipitated Halorhodopsin-containing cell membrane fragments from an aqueous solution of *E. coli* proteins with the highly hydrophobic chelators: bathophenanthroline, Phen-C10 or Phen-C8. SDS-PAGE analysis of pellets of aggregated membrane fragments showed that the pellets obtained following precipitation of the membrane fragments from the aqueous suspension, contained Halorhodopsin whereas most of the *E. coli* proteins (>85%, by densitometry) were excluded (FIG. 1B).

These results demonstrate that separation of a membrane protein from soluble proteins can be achieved in the absence of detergent, thereby preventing potential denaturation of the membrane protein. Whereas the commercially available bathophenanthroline led to higher recovery yields (82-89%, by densitometry) the two synthesized chelators, Phen-C10 and Phen-C8, led to 74-79% and 31-38% recovery, respectively, but provided greater purity (FIG. 1B lanes 3-5), showing that the structure of the chelator used is a major factor in the purification process, affecting both purity and yield.

It was further found that the pellets of the aggregated Halorhodopsin-containing membrane fragments could be readily dissolved with relatively low concentrations of several non-ionic detergents (e.g. 8 mM DDM, 14 mM DM, 18 mM OTG and 46 mM OG) while maintaining Halorhodopsin in its native state (FIGS. 2 A-D). Measurement of the absorption spectra of the dissolved pellets showed that the characteristic absorption of the retinal moiety at 578 nm was preserved as well as the ratio of the beta-carotene and the retinal chromophores (2.2:1, respectively).

Thus, the present inventors have shown that the methods disclosed herein provide a high level of separation of non-membrane cellular proteins from membrane proteins, resulting in high recovery yields and overall greater purity of the membrane protein.

Thus, according to a first aspect of the present invention there is provided a method of precipitating cell membrane fragments from a cell lysate, the method comprising contacting the cell lysate with a hydrophobic chelator and a metal ion under conditions that allow precipitation of the cell membrane fragments.

As used herein, the term "cell lysate" refers to an aqueous solution of cellular biological material, wherein a substantial portion of the cells of the cellular material have become disrupted and released their internal components.

In one embodiment, the cell lysate is prepared from whole cells. In another embodiment, the cell lysate may be prepared from a cellular organelle, such as a nuclear cell lysate.

In the case of a whole cell lysate, it will be appreciated that following cell membrane disruption, the cell lysate may be treated so as to remove organelles greater than about 2 microns (e.g. cell nucleii). Thus, for example the whole cell lysate may be centrifuged so as to precipitate cell nucleii from the cell lysate. Exemplary centrifugation conditions include 1-5 minutes at 500-1000×g (e.g. 2 min at 985×g).

In one embodiment, the cell lysate is a whole cell lysate which comprises cell membrane fragments.

In another embodiment, the cell lysate is a nuclear lysate which comprises nuclear membrane fragments.

The phrase "cell or nuclear membrane fragments" refers to membranes which are no longer intact (i.e. have been disrupted).

In some embodiments, the cell membrane fragments are provided as a suspension in the cell lysate.

Preferably, the cell or nuclear membrane fragments (or patches) have a length between 200-700 nm.

The cell lysate may be prepared from any cell. The cells may be eukaryotic (e.g. mammalian, plant, fungus) or prokaryotic (bacteria).

The bacteria may be a gram positive or a gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*,

*Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

In another embodiment, the cells are archae cells, such as *halobacterium* cells. Examples of *halobacterium* include *Halobacterium salinarum, Haloferax denitrificans, Alorubrum distributum, Alobacterium salinarum, Halobacterium jilantaiense, Halorubrum lacusprofundi, Haloferax mediterranei, Halobacterium noricense, Natronomonas pharaonis, Halobacterium piscisalsi, Halorubrum saccharovoru, Halobacterium salinarum, Halorubrum sodomense, Halorubrum trapanicum, Haloarcula vallismortis* and *Halobacterium volcanii.*

In one embodiment, the cells have been immortalized and are part of a cell line.

In another embodiment, the cells are part of a tissue preparation or an organism.

The cells may have been cultured (e.g. propagated) or taken directly from the cellular source without culturing.

The cell may be genetically modified so as to express the membrane protein. In another embodiment, the cell is not genetically modified.

There are a variety of ways to lyse cells. Well-known methods used include free-thawing, heat treatment, pressure treatment, mechanical grinding, sonication, treatment with chaotropes (e.g. guanidinium isothiocyante), non-ionic surfactants (e.g. Triton X100) and treatment with organic solvents (e.g. phenol).

It will be appreciated that the cell lysate is prepared such that the membrane proteins remain attached to (e.g. embedded in) the membrane and that non-membrane proteins do not become attached to the membrane during the process.

According to a particular embodiment the cell lysate is prepared without the use of chemical agents such as chaotropes or organic solvents.

As mentioned, the precipitation method of this aspect of the present invention is carried out by contacting the cell lysate with a hydrophobic chelator and a metal ion.

As used herein, the term "chelator" refers to a compound which binds metal ions from solution, by the formation or presence of two or more separate co-ordinate bonds between a polydentate ligand and a single central atom.

The chelator of this aspect of the present invention is capable of chelating the metal ion which is used for the precipitation. Preferably, the chelator binds electrostatically (non-covalently) to the metal ion. According to a particular embodiment, the chelator is capable of chelating metal ions with a ratio of chelator to metal of 2:1 or greater.

The hydrophobicity of the chelator is such that it is capable of partitioning into a hydrophobic environment of a cell membrane. In one embodiment, the chelator is capable of embedding into the lipid bilayer of the cell membrane. In another embodiment, the chelator binds to the lipids of the cell membrane fragment.

In one embodiment, the hydrophobic chelator comprises at least 8 carbons (for example in a chain, or in a ring) and does not comprise charged groups.

In some embodiments, the hydrophobic chelator is 8-Hydroxyquinoline or a derivative thereof.

Exemplary derivatives of 8-Hydroxyquinoline include, but are not limited to 2-methyl-8-hydroxyquinoline (CH3-HQ), 5,7-dichloro-2-methyl-8-hydroxyquinoline (Cl2-CH3-HQ), 5,7-dibromo-8-hydroxyquinoline (Br2-HQ), 5-sulfo-7-iodo-8-hydroxyquinoline (ferron) and 5-sulfo-8-hydroxyquinoline (SO3H-HQ).

In some embodiments, the hydrophobic chelator comprises a phenanthroline, for example a 1,10-Phenanthroline. Other phenanothrolines are also contemplated which have not been substituted with hydrophilic substituents.

Exemplary hydrophobic phenanthrolines include, but are not limited to bathophenanthroline, and N-(1,10-Phenanthrolin-5-yl)alkylamide), with the alkyl being from 1-10 carbon atoms in length. Exemplary N-(1,10-Phenanthrolin-5-yl)alkylamide) compounds include N-(1,10-Phenanthrolin-5-yl)methanamide) (Phen-C1), N-(1,10-Phenanthrolin-5-yl)ethanamide) (Phen-C2), N-(1,10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), N-(1,10-Phenanthrolin-5-yl)nonanamide) (Phen-C9), N-(1,10-Phenanthrolin-5-yl)decanamide) (Phen-C10).

In some such embodiments, the phenanthroline is selected from the group consisting of bathophenanthroline, N-(1,10-Phenanthrolin-5-yl)hexanamide) (Phen-6), N-(1,10-Phenanthrolin-5-yl)decanamide) (Phen-C10) and N-(1,10-Phenanthrolin-5-yl)octanamide) (Phen-C8).

Herein throughout, an "alkylamide" describes a —NH—C(=O)—R, wherein R is alkyl.

The term "alkyl" describes a saturated aliphatic hydrocarbon including straight chain and branched chain groups. Preferably, the alkyl group has 1 to 20 carbon atoms in length. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. The alkyl group may be substituted or unsubstituted. Substituted alkyl may have one or more substituents, whereby each substituent group can independently be, for example, alkyl, cycloalkyl, alkenyl, alkynyl, aryl, and heteroaryl. Additional substitutents may include, for example, hydroxyalkyl, trihaloalkyl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine, as long as the functionalities of the chelator are maintained.

In some preferred embodiments, the phenanthroline is Phen-C10 or Phen-C8.

Additional examples of hydrophobic chelators include acidic organophosphorus chelators, for example DEHPA, EHEHPA and DTMPPA; neutral organophosphorus chelators, for example TBP and tri-n-octylphosphine oxide (TOPO), bifunctional organophosphorus chelators, for example CMPO and N,N,N',N'-tetraoctyl-3-oxamentanediamide (TOGDA); basic chelators, for example tri-n-octylamine (TOA) and tricaprylmethylammonium chloride. Other chelators known to those of skill in the art may also be used, including hydroxyoximes, for example 5,8-diethyl-7-hydroxy-6-dodecane oxime and 2-hydroxy-5-nonylacetophenon oxime, crown ethers, for example di-t-butyl-dicyclohexano-18-crown-6, and dithiosemicarbazone.

According to some embodiments, the hydrophobic chelator is present in the aqueous solution at a concentration in the range of about 5% to about 10% (v/v), such as, for example, about 5%, about 6%, about 7%, about 8%, about 9%, or about 10% of 20 mM solution of chelator.

In some embodiments, the metal ion is a divalent metal ion.

In some embodiments, the divalent metal ion is selected from the group consisting of $Zn^{2+}$, $Fe^{2+}$, $Mn^{2+}$, $Ni^{2+}$ and $Co^{2+}$.

Preferably, the divalent metal ion $Zn^{2+}$ or $Fe^{2+}$.

In some embodiments, the metal ion is present in the aqueous solution at a concentration in the range of about 5% to about 10% (v/v), such as, for example, about 5%, about 6%, about 7%, about 8%, about 9%, or about 10% of 50 mM solution of metal ion.

The incubation may be carried out at a temperature of about 0° C. to about 25° C. and more preferably from about 4° C. to about 25° C.

In some embodiments, contacting the cell membrane fragment with a hydrophobic chelator is performed prior to contacting with a metal ion.

The cell membrane fragments may be incubated with the hydrophobic chelator for a time of up to 10 minutes prior to contacting with the metal ion, such as for example, up to 1 minute, up to 2 minutes, up to 3 minutes, up to 4 minutes or up to 5 minutes.

In other embodiments, contacting the cell membrane fragments with a hydrophobic chelator is performed concomitantly to contacting with a metal ion.

In still further embodiments, the hydrophobic chelator is contacted initially with the metal ion and then subsequently with the cell membrane fragments.

The precipitation method of this aspect of the present invention is preferably carried out in the absence of detergents (or in a reaction which is substantially free of detergents).

In order to prevent precipitation of soluble proteins from being precipitated by the metal ions, the present inventors further contemplate addition of a hydrophilic chelator to the reaction mix so as to chelate (i.e. remove) any free unbound metal ion present in the system.

In some embodiments, the cell membrane fragments are contacted sequentially with the hydrophobic chelator, the metal ion and subsequently the hydrophilic chelator.

Examples of hydrophilic chelators include but are not limited to ethylenediaminetetraacetate (EDTA), ethylene glycol tetraacetate (EGTA), catechol, histidine and analogues thereof.

In one embodiment, the hydrophilic chelator is zwitterionic (i.e. possesses positive and negative charges) and is repelled from entering into a hydrophobic membrane aggregate.

Examples of zwitterionic hydrophilic chelators include ethylenediaminetetraacetate (EDTA), ethylene glycol tetraacetate (EGTA), histidine and analogues thereof.

Following a sufficient incubation time, the reactants form a complex. Once formed (seconds to hours), precipitation of the complex may be facilitated by centrifugation (e.g. ultracentrifugation), although in some cases (for example, in the case of large complexes) centrifugation is not necessary or very mild centrifugation can be used (so at to render the solution more dense—e.g. for 1-5 minutes at a speed of 1000-3000×g).

Following precipitation, the membrane protein may be purified.

As used herein, the term "membrane protein" refers to a protein that is associated with a cell membrane.

According to one embodiment, the membrane protein is a transmembrane protein (e.g. a single transmembrane α-helix (bitopic membrane protein), a polytopic transmembrane α-helical protein or a polytopic transmembrane β-sheet protein).

According to another embodiment, the membrane protein is a peripheral membrane protein. Such proteins may interact with the cell membrane by an amphipathic α-helix parallel to the membrane plane (in-plane membrane helix); by a hydrophobic loop; by a covalently bound membrane lipid (lipidation); or by electrostatic or ionic interactions with membrane lipids (e.g. through a calcium ion).

The membrane protein may serve any function—e.g. a receptor, an ion pump, an ion channel or a carrier protein.

In one embodiment, the membrane protein is a retinyledene protein (e.g. channelrhodopsin, bacteriorhodopsin, halorhodopsin, or proteorhodopsin).

The halorhodopsin may be derived from any halobacteria (e.g. *Natronomonas pharaonis*).

Thus, according to another aspect of the present invention there is provided a method of purifying a membrane protein comprising:

(a) precipitating cell membrane fragments which comprise the membrane protein from a cell lysate according to the method described herein;

(b) isolating the cell membrane fragments following the precipitating; and (c) solubilizing the membrane protein, thereby purifying the membrane protein.

As used herein the term "purifying" refers to at least separating the membrane protein from non-membrane proteins.

Isolation of the membrane fragments is typically effected by removal of the supernatant from the precipitated membrane fragments.

The membrane fragments may then be solubilized using methods known in the art.

In one embodiment, the precipitated membrane protein is washed with free unmodified chelator which competes with the metal ion, thereby disrupting the complex.

Following the washing stage, the precipitated membrane fragments (and proteins expressed in same) are solubilized using a detergent.

In one embodiment, the detergent is a non-ionic detergent. Examples of non-ionic detergents include, but are not limited to decyl β-D-maltoside (DM), dodecyl β-D-maltoside (DDM), octyl β-D-glucoside (OG) and octyl β-D-1-thioglucoside (OTG).

It will be appreciated that whilst in some cases it may be desired to isolate and analyze the membrane fraction, the presently disclosed method can also be used to isolate the cytosolic protein fraction of the cell (i.e. removal of the cell membrane fraction).

Thus, according to another aspect of the present invention there is provided a method of purifying a cytosolic protein comprising:

(a) precipitating cell membrane fragments which comprise the membrane protein from a cell lysate according to the method described herein; and (b) removing the cell membrane fragments following the precipitating.

It will further be appreciated that the present method may also be used to purify (and subsequently analyze) agents which bind to membrane proteins. Since the presently described method is very quick and uses only very mild conditions, the method may be particularly appropriate for analyzing agents which break down very quickly and/or are very sensitive to harsh conditions. Such agents include for example neurotransmitters and neuropeptides.

Depending on the intended use of the protein (or protein fraction) that is isolated and optionally solubilized, the protein (either membrane or cytosolic) or agent that is bound thereto, may be subjected to further purification steps. This may be effected by using a number of biochemical methods which are well known in the art. Examples include, but are not limited to, fractionation on a hydrophobic interaction chromatography (e.g. on phenyl sepharose), ethanol precipitation, isoelectric focusing, reverse phase HPLC, chromatography on silica, chromatography on heparin sepharose, anion exchange chromatography, cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

In one embodiment, the protein which is isolated is crystallized.

As used herein the term "crystallizing" refers to the solidification of the molecule of interest so as to form a regularly repeating internal arrangement of its atoms and often external plane faces.

Several crystallization approaches which are known in the art can be applied to the sample in order to facilitate crystallization of the molecule of interest. Examples of crystallization approaches include, but are not limited to, the free interface diffusion method [Salemme, F. R. (1972) Arch. Biochem. Biophys. 151:533-539], vapor diffusion in the hanging or sitting drop method (McPherson, A. (1982) Preparation and Analysis of Protein Crystals, John Wiley and Son, New York, pp 82-127), and liquid dialysis (Bailey, K. (1940) Nature 145:934-935).

Presently, the hanging drop method is the most commonly used method for growing macromolecular crystals from solution; this approach is especially suitable for generating protein crystals. Typically, a droplet containing a protein solution is spotted on a cover slip and suspended in a sealed chamber that contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

In another embodiment, the protein is subjected to 2D gel electrophoresis.

The method of the present invention may be particularly useful for carrying out proteomic analysis of a membrane fraction of a cell. By removing non-relevant proteins from the sample prior to 2D gel electrophoresis analysis, the chance of eluting two proteins from a gel is decreased.

The agents used for precipitating the membrane fraction may be provided as a kit.

Thus, according to yet another aspect of the present invention there is provided a kit for precipitating cell membrane fragments comprising a hydrophobic chelator, a metal ion and at least one protease inhibitor.

Hydrophobic chelators and metal ions have been described herein above.

The hydrophobic chelator is preferably packaged in a separate container to the metal ion.

Protease inhibitors include serine protease inhibitors, cystein protease inhibitors aspartic protease inhibitors and metallo-protease inhibitors.

In one embodiment, the kit comprises at least two, at least three, at least four, at least five, at least six protease inhibitors.

Examples of protease inhibitors include, but are not limited to AEBSF, Bestatin, E-64, Pepstatin A, Phosphoramidon, Leupeptin and Aprotinin.

The protease inhibitors may be packaged separately or in a single container (i.e. as a cocktail).

Protease inhibitor cocktails are commercially available, for example from Sigma Aldrich.

The kit of this aspect of the present invention may comprise additional components useful for precipitation such as a hydrophilic chelator (as discussed herein above) and a detergent for solubilizing the membrane fraction (as discussed herein above).

Preferably, the containers of the kits of this aspect of the present invention include a label. Suitable containers include, for example, bottles, vials, syringes, and test tubes. The containers may be formed from a variety of materials such as glass or plastic.

In addition, other additives such as stabilizers, buffers, blockers and the like may also be added.

It is expected that during the life of a patent maturing from this application many relevant hydrophobic chelators will be developed and the scope of the term hydrophobic chelator is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Preparation of Purified Halorhodopsin

Materials and Methods
Reagents:

Bathophenathroline, octyl β-D-glucoside (OG), octyl β-D-1-thioglucoside (OTG), nonyl-β-D-glucoside (NG), decyl β-D-maltoside (DM), dodecyl β-D-maltoside (DDM), Sodium dodecyl sulfate (SDS), NaCl, $FeSO_4$, were obtained from Sigma-Aldrich (St. Louis, Mo.).

Synthesis of hydrophobic phenanthroline derivatives (Phen-C6, Phen-C8 and Phen C-10):

To a vigorously stirred saturated aqueous solution of $NaHCO_3$ (18 mL) at 0° C. was added 1,10-phenanthroline-5-amine (400 mg, 2.05 mmol) followed by hexanoyl chloride (0.350 mL, 337 mg, 2.5 mmol) or octanoyl chloride (0.432 mL, 407 mg, 2.5 mmol) or decanoyl chloride (0.515 mL, 477 mg, 2.5 mmol). After continued stirring until completion of the reaction (3 h, monitored by TLC), the mixture was extracted with ethyl acetate (3×10 mL). The organic layer was then treated with a few drops of pyridine and washed successively with 5% aqueous HCl (10 mL), 5% $NaHCO_3$ (10 mL) and water until neutral pH was achieved. The organic layer was dried over anhydrous $Na_2SO_4$ and concentrated in vacuo to provide the crude amide which was purified by silica gel column chromatography.

Characterization of phenanthroline derivatives N-(1,10-Phenanthrolin-5-yl)hexanamide) (Phen-C6):

Off-white solid; yield 490 mg, 82%; mp 72-74° C.; IR (KBr, $cm^{-1}$) 3261 (vs), 2954 (s), 2926 (vs), 2851 (m), 1660 (s), 1535 (vs), 1424 (m), 1318 (w), 1235 (w), 1190 (w), 1105 (w), 878 (w), 802 (w), 739 (s); $^1H$ NMR ($CDCl_3$, 500 MHz) δ 9.05 (d, J=4.3 Hz, 1H), 8.99 (d, J=4.3 Hz, 1H), 8.48 (d, J=8.4 Hz, 1H), 8.32 (d, J=8.0 Hz, 1H), 7.98 (s, 1H), 7.78 (dd, J=8.4, 4.3 Hz, 1H), 7.69 (dd, J=8.0, 4.3 Hz, 1H), 2.60 (t, J=7.5 Hz, 2H), 1.79 (quint, J=7.5 Hz, 2H), 1.45 (m, 4H), 0.98 (t, J=6.9 Hz, 3H); $^{13}C$ NMR ($CDCl_3$, 125 MHz) δ 176.2, 151.0, 150.7, 147.1, 145.3, 137.7, 133.1, 133.0, 129.9, 126.8, 125.1, 124.5, 123.0, 37.6, 32.8, 26.8, 23.7, 14.5; MS ($ES^+$, Ar) m/z (rel intensity) 295 ($[MH+1]^+$, 28), 294 ($MH^+$, 100); HRMS ($ES^+$, Ar) calcd for $C_{18}H_{20}N_3O$ ($MH^+$) 294.1606. found 294.1615.

N-(1,10-Phenanthrolin-5-yl)octanamide) (Phen-C8):

off-white solid; yield 505 mg, 77%; mp 83-85° C.; IR (KBr, $cm^{-1}$) 3259 (vs), 2954 (m), 2925 (s), 2851 (m), 1659 (vs), 1535 (vs), 1424 (m), 1312 (w), 1275 (w), 1236 (w), 1190 (w), 1107 (w), 972 (w), 878 (w), 802 (w), 739 (m); $^1H$ NMR ($CDCl_3$, 400 MHz) δ 8.94 (d, J=4.3 Hz, 1H), 8.87 (d, J=4.3 Hz, 1H), 8.35 (d, J=8.1 Hz, 1H), 8.11 (d, J=7.9 Hz, 1H), 7.77 (s, 1H), 7.61 (dd, J=8.1, 4.3 Hz, 1H), 7.54 (dd, J=7.9, 4.3 Hz, 1H), 2.55 (t, J=7.4 Hz, 2H), 1.76-1.71 (m, 2H), 1.29-1.40 (m, 8H), 0.90 (t, J=5.9 Hz, 3H); $^{13}C$ NMR ($CDCl_3$, 100 MHz) δ 176.0, 150.7, 150.4, 146.7, 144.8, 137.4, 132.8, 132.6, 129.5, 126.4, 124.8, 124.2, 122.6, 37.6, 33.0, 30.5, 30.2, 27.0, 23.8, 14.6; MS ($ES^+$, Ar) m/z (rel intensity) 323 ($[MH+1]^+$, 30), 322 ($MH^+$, 100); HRMS ($ES^+$, Ar) calcd for $C_{20}H_{24}N_3O$ ($MH^+$) 322.1919. found 322.1907.

N-(1,10-Phenanthrolin-5-yl)decanamide) (Phen-C10):

Has been characterized previously [Patchornik, G., Namboothiri, I.-N.-N., Nair, D.-K., Persky, R. (2012) Tethered non-ionic micelles: a matrix for enhanced solubilization of lipophilic compounds. Soft Matter, 8, 8456-8463].

Preparation of Halorhodopsin:

Halorhodopsin was produced from the ur KM-1 strain of *Natronomonas pharaonis* as described by Ihara et al. [Ihara, K., Narusawa, A., Maruyama, K., Takeguchi, M., and Kouyama, T. (2008) A halorhodopsin-overproducing mutant isolated from an extremely haloalkaliphilic archaeon *Natronomonas pharaonis. FEBS Lett.* 582, 2931-2936]. In brief, the cells were grown under illumination for two weeks in a culture medium at pH 9 containing 1 g $KH_2PO_4$, 1 g KCl, 1 g $NH_4Cl$, 200 mg $MgSO_4.7H_2O$, 200 g NaCl, 1 g monosodium glutamate, 5 g casamino acids, 5 g yeast extract, 15 g $Na_2CO_3$, and trace metals (1 µL HCl (32%), 0.2 mg $FeCl_2.4H_2O$, 0.025 mg $CoCl_2.6H_2O$, 0.01 mg $MnCl_2.4H_2O$, 7 µg $ZnCl_2$, 0.6 µg $H_3BO_3$, 4 µg $Na_2MoO_4.2H_2O$, 7 µg $NiCl_2.6H_2O$, 0.2 µg $CuCl_2.2H_2O$, 2.5 µg $AlCl_3$, 0.6 µg $Na_2WO_4.2H_2O$, 2.5 µg $AlCl_3$, 0.6 µg $Na_2WO_4.2H_2O$).

Cell pellets were prepared by centrifugation, suspended in basal salt medium and frozen overnight. The following day, the cell pellets were thawed, then treated with DNase at room temperature for a few hours followed by dialysis for two days. The cell debris was then removed by fast centrifugation. The supernatant was collected and washed with 100 mM NaCl several times to remove the excess bacterioruberin. Finally, the membranes were suspended in 100 mM NaCl.

Purification of Halorhodopsin:

Into an aqueous mixture containing: double distilled water (60 µl), 0.8M NaCl (50 µl), *E. coli* lysate (20 µl, as an artificial contamination background to demonstrate the efficacy of the embodiment), Halorhodopsin (30 µl of 0.2 mg\ml, present in the membrane fragments contained in the supernatant from the preceding section), 10 µl of either: bathophenanthroline, Phen-C10 or Phen-C8 (all at 20 mM in MeOH) were added with constant vigorous vortexing. After a short incubation (2 minutes) at room temperature (or 4° C.), 10 µl of 50 mM $ZnCl_2$ and 10 µl of 0.5M EDTA (pH=7.5) were added sequentially with constant vortexing. Samples were centrifuged for 3 minutes at 1537×g and the majority of the supernatant (160 µl) was discarded. Pellets were resuspended by addition of 160 µl of 50 mM EDTA (pH=7.5), centrifuged at 6150×g for 2 min and the supernatant discarded. Washed pellets were then dissolved with sample buffer, by vortexing or by crushing with a pipette tip, and analyzed by sodium dodecyl sulfate polyacrylamide gel electrophoresis (SDS-PAGE). For spectral analysis, pellets were dissolved with 50-200 µl of either: 14 mM DM, 8 mM DDM, 46 mM OG or 18 mM OTG in DDW.

Uv Spectroscopy:

Absorption measurements were performed using the HP 8453 UV-Vis spectrophotometer.

Light Microscopy:

Light microscope images were obtained using an Olympus CX40 microscope.

Densitometry:

The density of bands in the gels was quantified using the ImageJ (NIH) image analysis program.

Results

Purification of Halorhodopsin proteins embedded in native membranes was performed using one of three hydrophobic chelators (bathophenanthroline, Phen-C10 or Phen-C8) in the presence of $ZnCl_2$ without the use of detergent, using the method schematically illustrated in FIG. 1A.

It was found that Halorhodopsin-containing cell membrane fragments could be efficiently precipitated from aqueous solution after a brief incubation (2 min) with one of the above hydrophobic chelators followed by the addition of $Zn^{2+}$. SDS-PAGE analysis of the resulting pellets showed that most of the protein impurities from the *E. coli* lysate (>85% by densitometry) were removed by all three chelators tested. However, the two synthesized chelators (Phen-C10, Phen-C8) were found to provide purer samples than the commercially available bathophenanthroline (FIG. 1B, lanes 4-5 vs. 3).

The presence of EDTA (10-50 mM) after the addition of $Zn^{2+}$ and during the washing step of the pellet was found to substantially increase Halorhodopsin purity and therefore was used in all experiments. Similar results were also observed with $FeSO_4$ under identical conditions (not shown). Recovery yields of Halorhodopsin with bathophenanthroline, Phen-C10 and Phen-C8 were: 82-89%, 74-79% and 31-38%, respectively (by densitometry) (FIG. 1B, lanes 3-5).

Absorption Spectrum of Halorhodopsin Following Pellet Dissolution:

The absorption spectrum of Halorhodopsin was measured in the [(bathophenanthroline)$_3$:$Zn^{2+}$] complex, and following pellet dissolution by each of 4 different nonionic detergents (FIGS. 2A-D). Characteristic absorption of the native Halorhodopsin at 578 nm and the absorption of the carotenoid chromophore including its fine structure were essentially preserved with all four non-ionic detergents tested (FIGS. 2A-D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of precipitating fragments of a cell membrane out of a cell lysate, said fragments having a membrane protein attached thereto, said fragments having a length ranging between 200-700 nm, the method comprising contacting the fragments of the cell membrane with a hydrophobic chelator and a metal ion(s) to generate a complex which comprises said fragments of the cell membrane, said hydrophobic chelator and said metal ions, wherein said contacting is effected in the absence of a detergent, thereby precipitating fragments of a cell membrane.

2. The method of claim 1, wherein said fragments are generated by sonicating whole cells.

3. The method of claim 1, wherein said cell lysate is a whole cell lysate.

4. The method of claim 1, wherein said cell lysate is devoid of organelles greater than about 2 microns.

5. The method of claim 1, further comprising centrifuging said cell lysate so as to isolate said fragments from said cell lysate following said precipitating.

6. The method of claim 5, further comprising solubilizing said membrane protein of said fragments following said centrifuging.

7. The method of claim 6, wherein said solubilizing is effected with a detergent.

8. The method of claim 6, wherein said detergent is a non-ionic detergent.

9. The method of claim 6, wherein said detergent is selected from the group consisting of decyl β-D-maltoside (DM), dodecyl β-D-maltoside (DDM), octyl β-D-glucoside (OG) and octyl β-D-1-thioglucoside (OTG).

10. The method of claim 1, wherein said hydrophobic chelator is 8-Hydroxyquinoline.

11. The method of claim 1, wherein said hydrophobic chelator is a phenanthroline.

12. The method of claim 11, wherein said phenanthroline is selected from the group consisting of N-(1,10-Phenanthrolin-5-yl)methanamide) (Phen-C1), N-(1,10-Phenanthrolin-5-yl)ethanamide) (Phen-C2), N-(1,10-Phenanthrolin-5-yl)propanamide) (Phen-C3), N-(1,10-Phenanthrolin-5-yl)butanamide) (Phen-C4), N-(1,10-Phenanthrolin-5-yl)pentanamide) (Phen-C5), N-(1,10-Phenanthrolin-5-yl)hexanamide) (Phen-C6), N-(1,10-Phenanthrolin-5-yl)heptanamide) (Phen-C7), N-(1,10-Phenanthrolin-5-yl)octanamide) (Phen-C8), N-(1,10-Phenanthrolin-5-yl)nonanamide) (Phen-C9) and N-(1,10-Phenanthrolin-5-yl)decanamide) (Phen-C10).

13. The method of claim 11, wherein said phenanthroline is selected from the group consisting of bathophenanthroline, N-(1,10-Phenanthrolin-5-yl)hexanamide) (Phen-6), N-(1,10-Phenanthrolin-5-yl)decanamide) (Phen-C10) and N-(1,10-Phenanthrolin-5-yl)octanamide) (Phen-C8).

14. The method of claim 13, wherein said phenanthroline is selected from the group consisting of Phen-C10 and Phen-C8.

15. The method of claim 1, wherein said metal ion is a divalent metal ion.

16. The method of claim 15, wherein said divalent metal ion is selected from the group consisting of $Zn^{2+}$, $Fe^{2+}$, $Mn^{2+}$, $Ni^{2+}$ and $Co^{2+}$.

17. The method of claim 16, wherein said divalent metal ion is selected from the group consisting of $Zn^{2+}$ and $Fe^{2+}$.

18. The method of claim 1, wherein said contacting said cell lysate with a hydrophobic chelator is effected prior to said contacting said cell lysate with said metal ion.

19. The method of claim 1, wherein said cell lysate is further contacted with a hydrophilic chelator following or concomitant with said contacting with said hydrophobic chelator.

20. The method of claim 19, wherein said hydrophilic chelator is selected from the group consisting of ethylenediaminetetraacetate (EDTA), ethylene glycol tetraacetate (EGTA) and histidine.

21. The method claim 20, wherein said hydrophilic chelator comprises ethylenediaminetetraacetate (EDTA).

22. The method of claim 1, wherein said hydrophobic chelator is present at a concentration in the range of about 5% to about 10% (v/v).

23. The method of claim 1, wherein said metal ion is present at a concentration in the range of about 5% to about 10% (v/v).

24. The method of claim 1, wherein said cell lysate is derived from a bacterial cell.

25. The method of claim 1, wherein said cell lysate is derived from an archaeal cell.

26. The method of claim 25, wherein said archaeal cell is a *halobacterium* cell.

27. The method of claim 26, wherein said *halobacterium* is selected from the group consisting of *Halobacterium salinarum, Haloferax denitrificans, Alorubrum distributum, Alobacterium salinarum, Halobacterium jilantaiense, Halorubrum lacusprofundi, Haloferax mediterranei, Halobacterium noricense, Natronomonas pharaonis, Halobacterium piscisalsi, Halorubrum saccharovoru, Halobacterium salinarum, Halorubrum sodomense, Halorubrum trapanicum, Haloarcula vallismortis* and *Halobacterium volcanii*.

* * * * *